United States Patent [19]
Ross et al.

[11] Patent Number: 5,466,897
[45] Date of Patent: Nov. 14, 1995

[54] STETHOSCOPE DIAPHRAGM DISPENSER AND METHOD

[75] Inventors: James B. Ross, Livermore; Gary L. Christiansen, Mountain View; Ronald Chang, Redwood City, all of Calif.

[73] Assignee: Modern Medical Devices, Fremont, Calif.

[21] Appl. No.: 255,481

[22] Filed: Jun. 8, 1994

[51] Int. Cl.⁶ .................................................. A61B 7/02
[52] U.S. Cl. ........................................ 181/131; 221/266
[58] Field of Search .............................. 181/131, 137; 221/175, 176, 263, 266

[56] References Cited

U.S. PATENT DOCUMENTS 2,499,969  3/1950  Quintrell ................................ 221/176
3,587,924  4/1969  Diorio .................................. 221/266 X
4,867,268  9/1989  Ulert ...................................... 181/131

*Primary Examiner*—Khanh Dang
*Attorney, Agent, or Firm*—Peter J. Dehlinger

[57] ABSTRACT

A dispenser apparatus for use in dispensing disposable stethoscope diaphragms for removable attachment to a stethoscope head is disclosed. The apparatus operates by removing a diaphragm from a stack, and presenting it for attachment to a stethoscope, when a dispensing plate is shuttled between retracted and extended positions. Also disclosed is a method for reducing the risk of infection by stethoscope use.

6 Claims, 5 Drawing Sheets

STETHOSCOPE DIAPHRAGM DISPENSER AND METHOD

1. Field of the Invention

The present invention relates to a stethoscope diaphragm dispenser, and to a method of reducing the risk of infection by stethoscope use.

2. References

Brandenburg, U.S. Pat. No. 2,651,380 (1953).
Ersek, U.S. Pat. No. 3,867,925 (1975).
Hasbrouck, U.S. Pat. No. 3,255,841 (1966).
Mangi, et al., *Yale J. of Biol. & Med.* 45,600–45,604 (1972).

3. Background of the Invention

A stethoscope is used frequently in a doctor's office, in hospital clinics, and in emergency settings for medical examination purposes. Typically, the stethoscope is applied to the skin of the neck, chest, back or inguinal portions of the patients. During such an examination, the diaphragm becomes contaminated with skin bacteria and the like, which can then be transmitted to the next patient unless the portions of the diaphragm which are in contact with a patient are sterilized after each use. The problem if transmission of bacterial infections among patients, particularly in a hospital setting, has been aggravated by the development of antibiotic-resistant strains of staphylococcal infections.

The use of disposable diaphragms or diaphragm coverings for stethoscopes has been proposed as a solution to this problem. U.S. Pat. No. 4,867,268, for example, discloses a thin-plate disposable diaphragm that, when releasably attached to a stethoscope head ring, functions as the diaphragm in the stethoscope. Other disposable diaphragm members that can be releasably attached to a stethoscope head have been proposed. One limitation of disposable diaphragms of this type is the need to modify existing diaphragms by removing the membrane normally supplied with the stethoscope, leaving the stethoscope internal plate more susceptible to damage or harboring infection.

This problem has been partially overcome by a disposable diaphragm cap that can be releasably attached to a stethoscope head, and which provides a flexible covering for the stethoscope membrane. One such cap is disclosed in U.S. Pat. No. 4,461,368. This cap is constructed of two different polymer materials, a relatively stiff rim material, and an elastomeric covering material, and is thus more difficult and expensive to manufacture than a single-material cover. Furthermore, the elastomeric covering material may dampen the vibrational response of the underlying stethoscope membrane, causing loss of performance.

It would also be desirable to provide a dispenser device for dispensing such disposable diaphragms or covers. Such as dispenser should be easy to load and operate, reliable, and allow releasable attachment of diaphragms to a stethoscope without risk of contamination.

4. Summary of the Invention

The present invention includes, in one aspect, a dispenser for use in dispensing disposable stethoscope diaphragms for removable attachment to a stethoscope head, where the diaphragms are supplied in a stacked array in a tube. The apparatus includes a base defining an opening for receiving such diaphragms therethrough, and structure on said base for supporting such a tube in an upright position. The structure is positioned with respect to said opening to allow a diaphragm in the tube immediately adjacent the opening to be received through the opening, when a tube is supported on the base.

The diaphragms are dispensed by a plate slidably mounted on the base for movement between retracted and extended positions. A cradle formed in the plate receives a single diaphragm through said opening, when the dispensing plate is in its retracted position. Movement of the dispensing plate from its retracted to extended position is effective to place a diaphragm in the plate cradle in a position that allows the diaphragm to be attached to a stethoscope head by pressing the stethoscope head against the diaphragm.

In a preferred embodiment, the cradle defines a lower, reduced-diameter region for receiving a diaphragm, and an upper, increased-diameter region for receiving a stethoscope head, when such is pressed against a diaphragm in the cradle. The bottom of the cradle may include an opening for receiving therethrough, a tab associated with the tube, when the tube is placed in the receiving means. This allows the diaphragms in the tube to be released for gravity-feed dispensing.

Also disclosed is a dispenser apparatus for use in dispensing disposable stethoscope diaphragms for removable attachment to a stethoscope head. The apparatus includes, in combination, a dispenser of the type just described and a tube containing such diaphragms in a stacked array in the tube. The tube is received in the supporting structure in the dispenser for dispensing diaphragms by gravity feed, as the dispenser plate is moved alternatively between its retracted and extended positions.

In another aspect, the invention includes a method of reducing the risk of the spread of infection by stethoscope use, where the stethoscope has a head composed of a cup, a flat membrane, and a ring holding the membrane on the cup. The method includes mounting on the ring, a disposable diaphragm having (i) a semi-rigid elastomeric membrane disk with a preferred thickness between about 5 and 25 mils, (ii) a semi-rigid annular rim formed integrally with the disk, and being adapted to be received on the ring of a stethoscope head, to attach the diaphragm releasably to the head, and (iii) a spacer effective to position the membrane disk adjacent the stethoscope membrane, with a preferred spacing of between about 1 and 50 mils.

The diaphragm is effective to protect the stethoscope membrane against contamination, without loss of stethoscope performance, and is replaced after each new-patient use.

These and other objects and features of the invention will become more fully appreciated when the following detailed description of the invention is read in conjunction with the accompanying drawings.

DETAILED DESCRIPTION OF THE INVENTION

A. Stethoscope Diaphragm and Method

Figure 1:
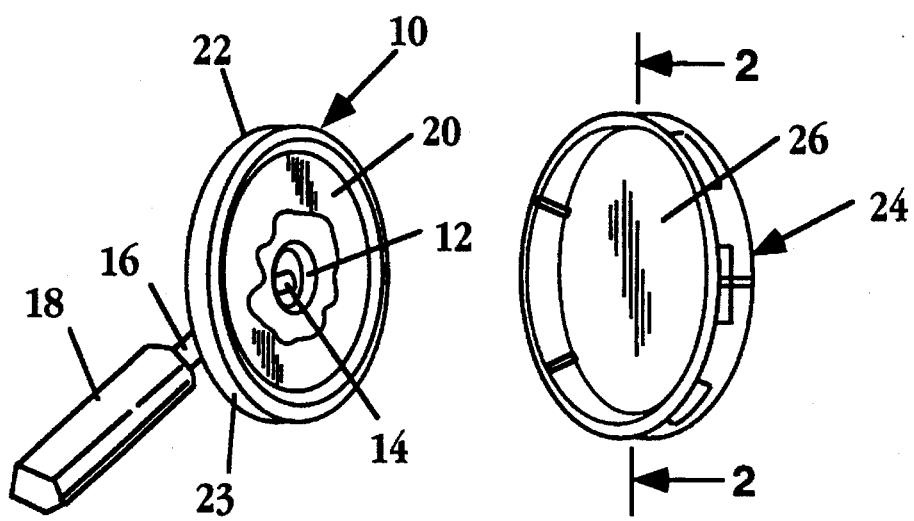
FIG. 1 is an exploded, perspective view of the combination of a stethoscope and a disposable diaphragm used to protect the stethoscope head from contamination.

FIG. 1 shows a stethoscope head 10 in a conventional stethoscope. The head generally includes shallow conical cup 12 which converges to a central cavity 14 that in turns feeds into a rigid tube 16. The rigid tube communicates with a flexible tube 18 that in turn is connected to a standard flexible headset in the stethoscope.

Cup 12 is covered by a thin, flexible membrane 20 which serves as the sound transducer in the stethoscope. The membrane is held against the outer edge of the cup by a ring 22 which is screwed onto an outer rim 23 of the head. During normal operation, the stethoscope membrane cup is placed against a patient, and can thus become contaminated with viral, bacterial or other infectious agents.

Figure 2:
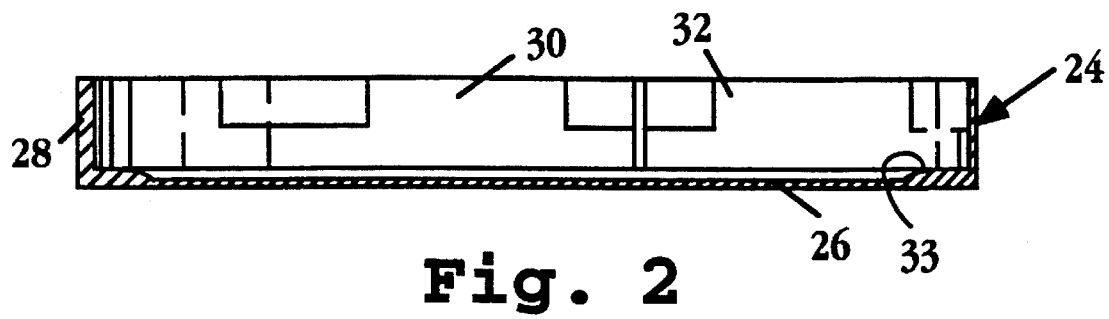
FIG. 2 shows a cross-sectional view of the FIG. 1 diaphragm, taken along line 2—2 in FIG. 1.

In accordance with one aspect of the invention, there is provided a method for protecting the stethoscope membrane against such contamination. The method includes mounting on the stethoscope ring, a disposable diaphragm 24 that is designed to be releasably attached to the stethoscope head. With reference to FIGS. 1 and 2, the diaphragm includes a semi-rigid membrane disc 26, having a preferred thickness between about 5 and 25 mils. Functionally, the disc acts as a vibrating membrane, much like the stethoscope's membrane, to transduce sound vibrations when the diaphragm is placed against a patient's skin.

Figure 3:
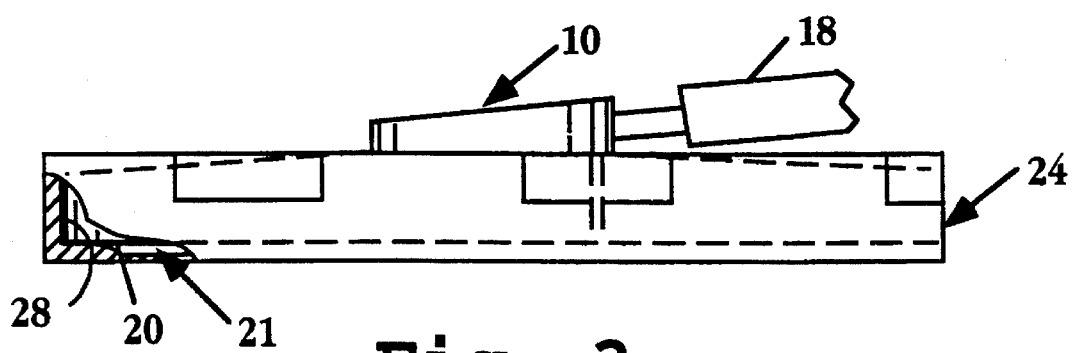
FIG. 3 shows a side view of the FIG. 1 stethoscope head equipped with a disposable diaphragm, in accordance with the invention.

The disc is supported by and integrally formed with a semi-rigid annular rim 28 which is adapted to be received on the ring of the stethoscope head, to attach the diaphragm releasably to the head, as illustrated in FIG. 3. The rim has a series of sections, such as sections 30 which are alternately thicker and less flexible, and thinner and more flexible, sections 32. This construction allows considerable deformation of the rim in fitting over different-size stethoscope rim, but with substantial retention of the rim strength.

With continued reference to FIGS. 2 and 3, the diaphragm also includes an annular step 33 which acts as a spacer for spacing the diaphragm's disk from the stethoscope membrane, with the diaphragm full received on the stethoscope rim, as shown in FIG. 3. The step is preferably dimensioned to produce a spacing 21 of between about 1 and 50 mils between the membrane 20 and disc 26, as seen in the cutaway portion of FIG. 3.

According to an important feature of the invention, it has been discovered that disk and membrane can act together in transducing picked by the diaphragm disc, without significant loss in sound volume or quality over the membrane alone, allowing the stethoscope to be used in combination with a disposable diaphragm that without having to remove the stethoscope membrane. At the same time, the semi-rigid diaphragm can function alone as the stethoscope sole membrane, if the stethoscope membrane has been removed.

The diaphragm is preferably formed as a unitary molded article from a thermoplastic polymer, such as polystyrene (ABS polymer), polypropylene, or polyethylene. Methods for preparing such molded articles are well known in the plastics field.

B. Diaphragm Dispenser and Apparatus

Also forming part of the invention is a dispenser for use in dispensing disposable stethoscope diaphragms, such as diaphragms of the type described above, for removable attachment to a stethoscope head.

Figure 4A:
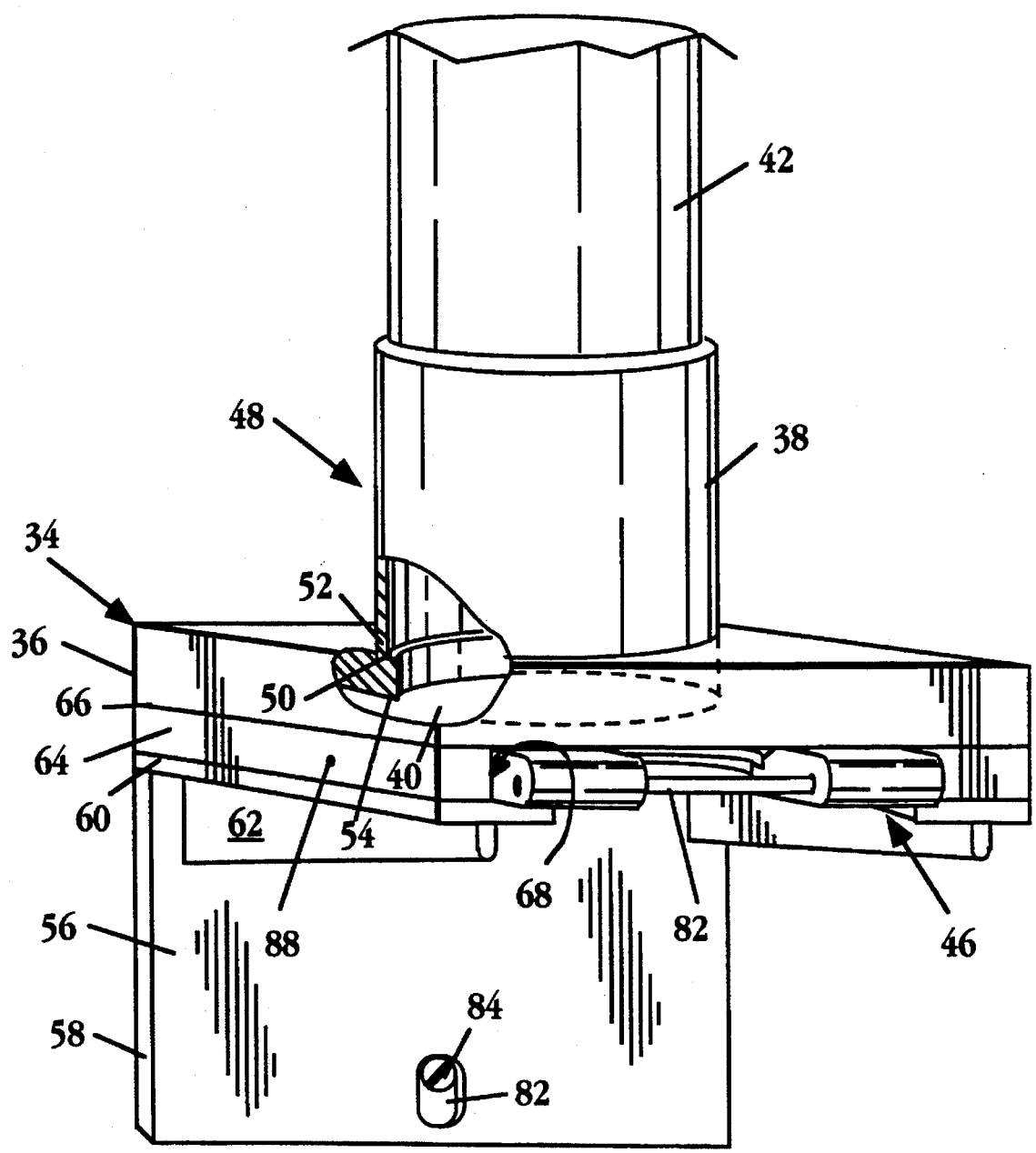
FIG. 4A and FIG. 4B are front perspective views of a dispenser (FIG. 4A) and dispenser apparatus (FIG. 4B) constructed in accordance with the invention, with the dispensing plate shown in its retracted, (FIG. 4A) and extended (FIG. 4B) positions.
Figure 4B:
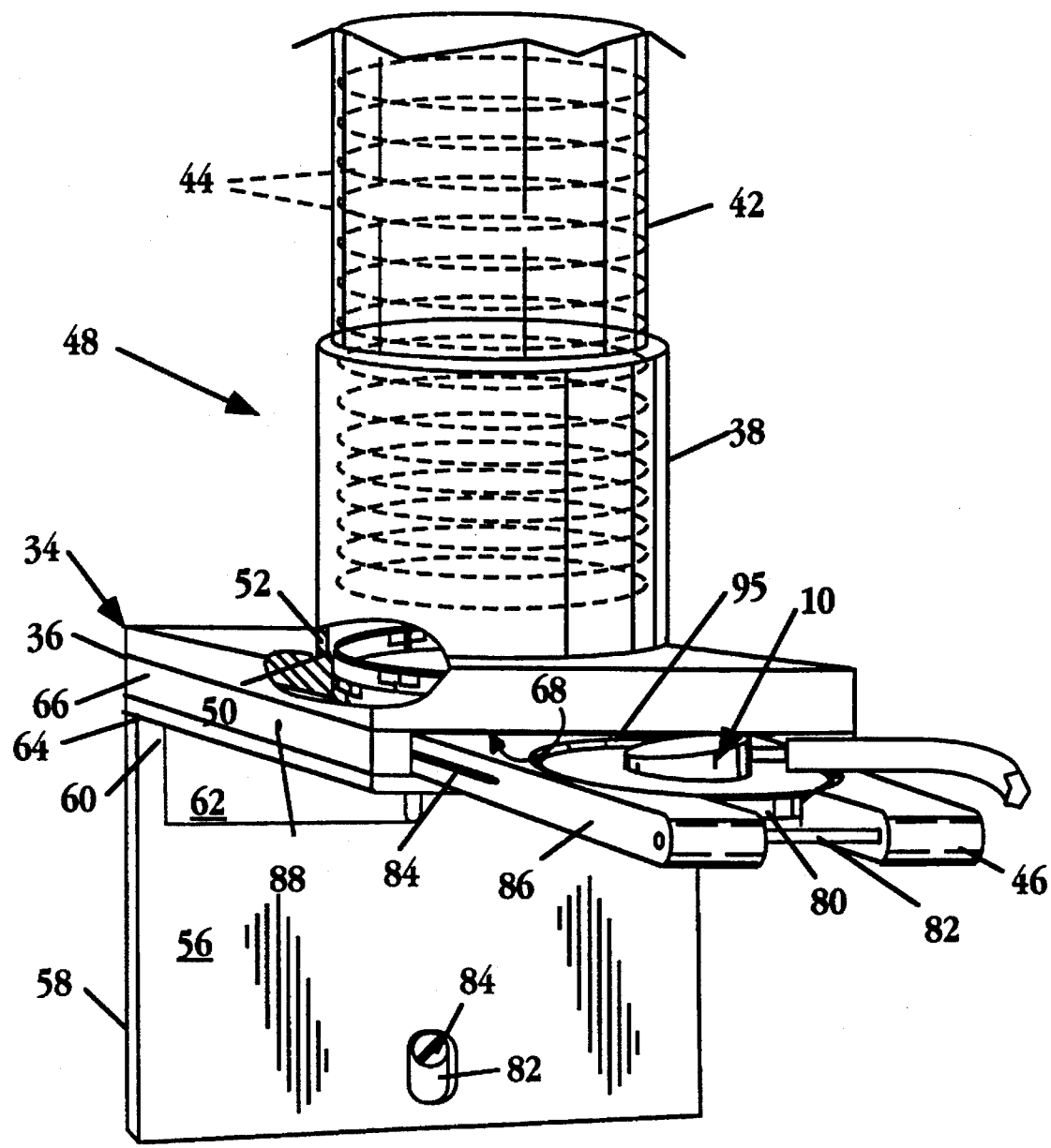

FIG. 4A shows a dispenser 34 constructed in accordance with the invention. The dispenser generally includes a base 36 defining an opening 40 for receiving diaphragms, such as diaphragms 44, indicated in FIG. 4B, therethrough. A tube support 38 mounted on the upper surface of the base is aligned with opening 40. As shown in FIG. 4B, the tube support is designed to hold a tube 42 that contains a plurality of diaphragms, such as diaphragms 44, which are to be dispensed, in a manner to be described. The tube support is also referred to herein as tube support means for supporting the tube in an upright position.

Also forming part of the dispenser is a dispensing plate 46 slidably mounted on the base for movement between retracted and extended positions, such as indicated in FIGS. 7A and 7B, respectively.

The dispenser in combination with the tube forms what is referred to herein as a dispenser apparatus, indicated generally at 48, illustrated in FIG. 4B.

Considering the construction of the dispenser, and with continued reference to FIG. 4A, the top of the opening 40 terminates at a ledge 50, which forms the bottom of a tubular recess 52 that communicates with the opening. This recess receives a lower edge portion of the tube support such that the lower edge of the support rests against ledge 50, with a portion of the ledge extending slightly beyond the inner surface of the tube support. This overhang, shown at 54 in FIG. 4A, provides a stop for supporting the bottom edge of tube 42 in the support, as shown. The tube support is dimensioned to receive therein a disposable tube loaded with diaphragms, such as diaphragms 44 indicated in FIG. 4B. In the operation described below, diaphragms from the tube fall by gravity feed through opening 40 into the dispensing plate, for dispensing.

With continued reference to FIG. 4B, base 36 is carried on a support structure 56 having a back plate 58 for mounting on a wall or the like, and a cantilevered lower base member 60 extending from the back plate and supported thereon by struts, such as strut 62. The support structure is typically formed as a unitary molded or cast article.

The base in the dispenser is formed of lower base member 60, a pair of intermediate spacers 64, and an upper base member 66. Upper base member 66 defines opening 40. The two base members and intermediate spacers, which are secured together by conventional means, form a channel 68 in which dispensing plate 46 is slidably received, and in which the plate slidably moves between its retracted and extended positions, as shown in FIGS. 4A and 4B, respectively.

Figure 5:
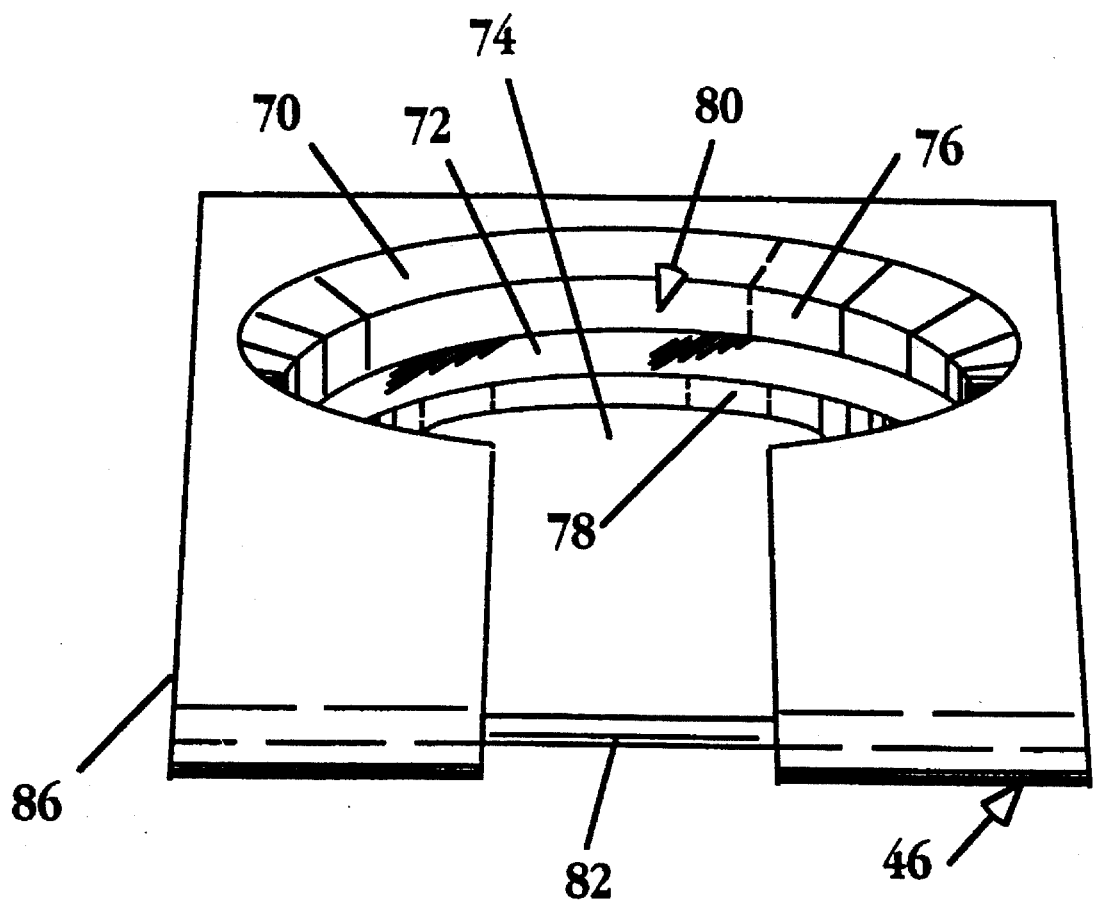
FIG. 5 is a detail view of a dispensing plate which forms part of the dispenser.

Details of the plate construction are seen in FIG. 5. Formed in a center region of the plate is a bevelled annular surface, 70, a reduced-diameter annular ledge 72, and a lower opening 74. Surface 70 and ledge 72 are connected by an annular wall 76 and opening 74 is defined by a smaller-diameter wall 78. Wall 76 and ledge 72 form a cradle 80 for receiving a diaphragm loosely therein, without appreciable frictional contact. The depth of the cradle, i.e., the distance between ledge 72 and the upper surface of the dispensing plate is just slightly greater than the sidewall of the diaphragm, to accommodate a diaphragm in the cradle such that the upper edge of the diaphragm is just slightly below the plane of the plate's upper surface.

A front section of dispensing plate 46 is cut out, and provided with a pull bar 82 to serve as a handle for the plate. Formed along opposite sides of the plate are grooves, such as groove 84 formed in side 86, which serve a purpose now to be described.

With continuing reference to FIG. 4B, with the plate mounted in the channel formed in base 36, pins, such as pin 88, extending through the associated spacer, engage the associated plate groove, allowing sliding movement of the plate between the retracted and extended positions, and preventing the plate from lateral movement beyond its extended positions, to hold the plate in the base.

Figure 6:
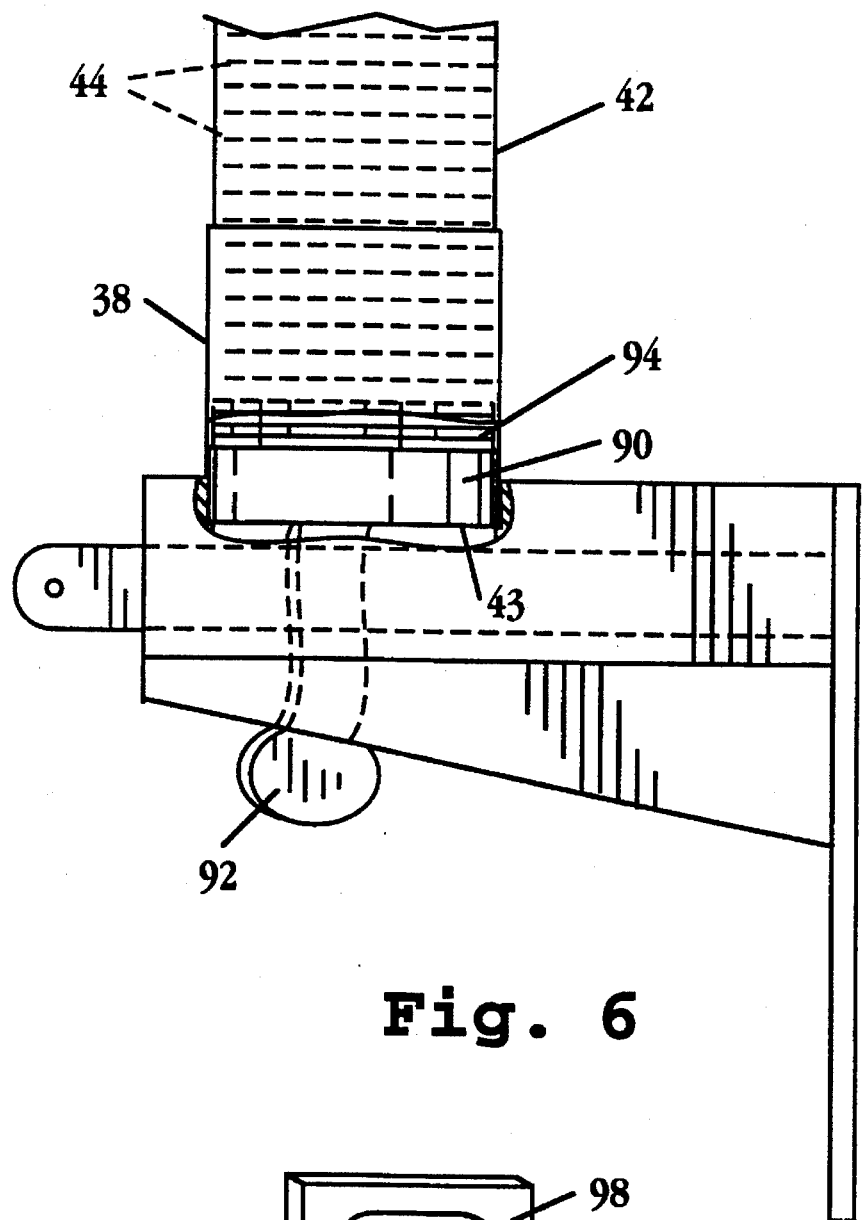
FIG. 6 shows a tab structure used for releasing diaphragms in a tube in the FIG. 4 apparatus for gravity feed.

Operation of the dispensing device can be appreciated with reference to FIGS. 6, 4A and 4B. With reference to FIG. 6, a tube, such as tube 42, having a lower open end 43 containing diaphragms 44 is placed in an upright position in tube support 38, such that the diaphragms are positioned in the support with their concave surfaces upward. As illustrated, tube 42 contains at its lower open end, a flexible holding ring 90 which serves as a restraining means for the diaphragms carried in the tube. The holding ring terminates in a pull tab 92 which is dimensioned to project downward from the tube through the openings in the base and the cradle, described above.

Diaphragms 44 are released for dispensing from the tube in the dispenser apparatus by exerting a downward force on the pull tab. This results in a downward displacement of diaphragms in tube 42 and releases lowermost diaphragm 94 into opening 40 where it drops by gravity to rest in cradle 80 formed in dispensing plate 46 when the dispensing plate is in a retracted position, as shown in FIG. 4A.

For dispensing a diaphragm, dispensing plate 46 is pulled outward from its retracted position in chamber 68 to an extended position, shown in FIG. 4B, by pulling out on pull bar 82. In this configuration of the dispenser, diaphragm 95 is in a position that allows it to be attached to a stethoscope head by pressing the stethoscope head against the diaphragm in the cradle.

Following the dispensing operation described above, dispensing plate 46 is pushed back into chamber 68, where it receives by gravity drop, another diaphragm from tube 42 through opening 40, as described above.

Figure 7:
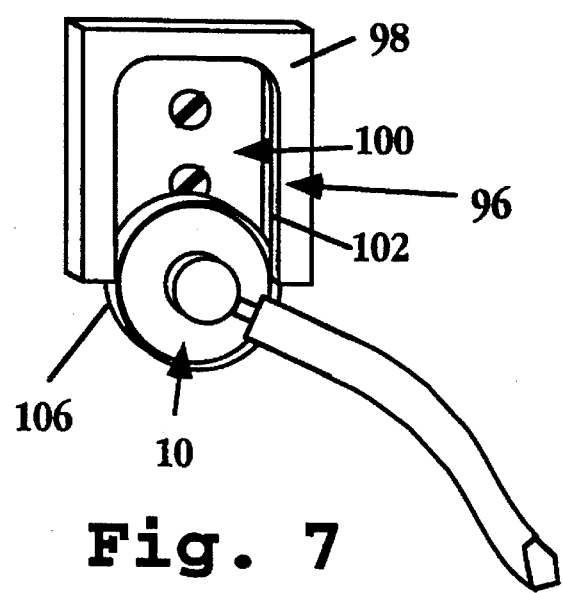
FIG. 7 shows a diaphragm-removal device in the dispenser apparatus.

An additional, optional feature of the device is a diaphragm removal device 96, illustrated in FIG. 7. Generally, the device comprises means defining a slotted opening adapted to receive and capture a diaphragm attached to a stethoscope head, to allow removal of the diaphragm from the head with minimal operator contact with the diaphragm. As shown in FIG. 7, the devise consists of a three-sided frame 98 forming a U-shaped opening 100. Opposing sides of the frame each contain a slot, such as slot 102. As shown in the cutaway portion of the figure, the slots form a horizontal opening across the frame that is slightly larger than the diameter of the diaphragm to be removed. Each slot has a depth that is slightly larger than the vertical dimension of the diaphragm 106. As will appreciated from the description of the operation of the removal device, below, such dimensions allow for sliding of the diaphragm into the opening, guided by the slots on either side of the opening.

In operation, stethoscope head 10 carrying a diaphragm 106 is inserted into slots 102, 104 in the lower end of frame 98 of the removal device. The stethoscope and attached diaphragm are then moved upward in the slots toward the top of the U-shaped opening, where the slots terminate, and the opening is too narrow to accommodate further upward movement of the diaphragm. The stethoscope is then twisted slightly outward with respect to the diaphragm to effect removal of the diaphragm from the stethoscope head.

Although the invention has been described with reference to particular embodiments and methods, it will be appreciated that various changes and modifications can be made without departing from the invention.

It is claimed:

1. In combination,
   a) a disposable stethoscope diaphragm for removable attachment to a stethoscope head;
   b) a dispenser for use in dispensing disposable stethoscope diaphragms, where the diaphragms are supplied in a stacked array in a tube, said dispenser comprising
      a base defining an opening for receiving such diaphragms therethrough,
      means on said base for supporting such a tube in an upright position, and positioned with respect to said opening to allow a diaphragm in the tube immediately adjacent said opening to be received through said opening, when such a tube is supported on the base by said means,
      a dispensing plate slidably mounted on said base for movement between retracted and extended positions, and
      a cradle formed in said plate for receiving a single diaphragm through said opening, when the dispensing plate is in its retracted position,
      wherein movement of the dispensing plate from its retracted to extended position is effective to place a diaphragm in said recess in a position that allows the diaphragm to be attached to a stethoscope head by pressing the stethoscope head against the diaphragm.

2. The dispenser of claim 1, wherein said cradle defines a lower, reduced-diameter region for receiving a diaphragm, and an upper, increased-diameter region for receiving a stethoscope head, when such is pressed against a diaphragm in thee cradle.

3. The dispenser of claim 1, wherein the bottom of said cradle include an opening for receiving therethrough, a tab associated with said tube, when the tube is placed in said receiving means.

4. The dispenser of claim 1, which further includes means defining a slotted opening adapted to receive and capture a diaphragm attached to a stethoscope head, to allow removal of the diaphragm from the head.

5. In combination,
   a) a disposable stethoscope diaphragm for removable attachment to a stethoscope head;
   b) a dispenser apparatus for use in dispensing disposable stethoscope diaphragms comprising
      a base defining an opening for receiving such diaphragms therethrough,
      a tube containing such diaphragms in a stacked array,
      means on said base for supporting said tube in an upright position, and positioned with respect to said opening to allow a diaphragm in the tube immediately adjacent said opening to be received through said opening, with said tube supported on the base by said means,
      a dispensing plate slidably mounted on said base for movement between retracted and extended positions, and
      a cradle formed in said plate for receiving a single diaphragm through said opening, when the dispensing plate is in its retracted position, wherein movement of the dispensing plate from its retracted to extended position is effective to place a diaphragm in said cradle in a position that allows the diaphragm to be attached to a stethoscope head by pressing the stethoscope head against the diaphragm.

6. The apparatus of claim 5, wherein the bottom of said cradle include an opening, and said tube, prior to being placed in said receiving means, includes a flexible holding ring for retaining diaphragms in said tube, when the tube is in an upright condition, and a tab attached to the holding ring, and receivable through said cradle opening, to allow the holding ring to be pulled from the tube, with the tube placed in said supporting ring.

* * * * *